US00PP36543P2

(12) United States Plant Patent
van Swieten

(10) Patent No.: US PP36,543 P2
(45) Date of Patent: Mar. 11, 2025

(54) ***PHALAENOPSIS* PLANT NAMED 'PHA899665'**

(50) Latin Name: *Phalaenopsis hybrida*
Varietal Denomination: PHA899665

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/769,925

(22) Filed: Jul. 11, 2024

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'PHA899665', characterized by its upright plant habit; vigorous growth habit and moderate to rapid growth rate; strong flowering stems; strong leaves; freely flowering habit with typically three inflorescences developing per plant, each inflorescence with numerous flowers; greenish yellow-colored flowers with purplish red-colored labellum; and good postproduction longevity.

2 Drawing Sheets

Figure 1:
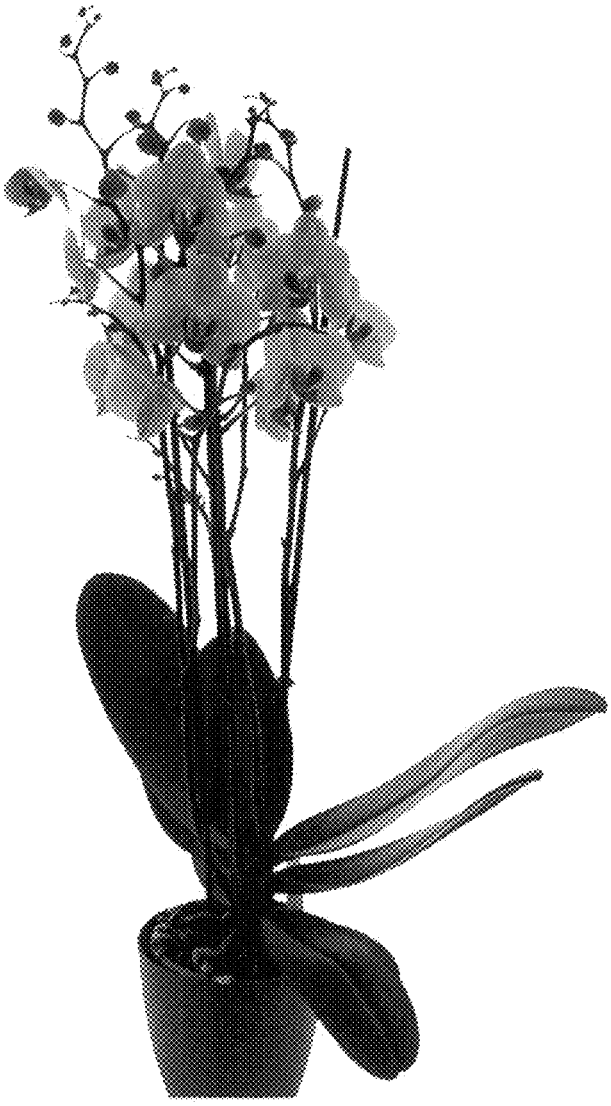

Botanical designation: *Phalaenopsis hybrida.*
Cultivar denomination: 'PHA899665'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Jan. 22, 2023, application number 2023/0209. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA899665'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique and attractive patterns and coloration.

The new *Phalaenopsis* plant originated from a cross-pollination in May, 2016 in Bleiswijk, The Netherlands of a proprietary selection of *Phalaenopsis hybrida* identified as code number 10-44838-02, not patented, as the female, or seed, parent with a proprietary selection of *Phalaenopsis hybrida* identified as code number 99-21232-04, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in March, 2019.

Asexual reproduction of the new *Phalaenopsis* plant by in vitro meristem propagation in a controlled environment in Bleiswijk, The Netherlands since March, 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA899665'. These characteristics in combination distinguish 'PHA899665' as a new and distinct *Phalaenopsis* plant:

1. Upright plant habit.
2. Vigorous growth habit and moderate to rapid growth rate.
3. Strong flowering stems.
4. Strong leaves.
5. Freely flowering habit with typically three inflorescences developing per plant, each inflorescence with numerous flowers.

6. Greenish yellow-colored flowers with purplish red-colored labellum.
7. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are horizontal in aspect whereas leaves of plants of the female parent selection are horizontal to semi-drooping in aspect.
2. Petals of plants of the new *Phalaenopsis* are greenish yellow in color whereas petals of plants of the female parent selection are yellow in color.
3. Petals of plants of the new *Phalaenopsis* do not have any stripes whereas petals of plants of the female parent selection are moderately striped.

Plants of the new *Phalaenopsis* can be compared to plants of the male parent selection. Plants of the new *Phalaenopsis* differ primarily from plants of the male parent selection in flower color as petals of plants of the new *Phalaenopsis* are greenish yellow in color whereas petals of plants of the male parent selection are white in color. In addition, the labella of plants of the new *Phalaenopsis* are purplish red in color whereas the labella of plants of the male parent selection are greenish yellow and white in color.

Plants of the new *Phalaenopsis* can be compared to plants of *Phalaenopsis hybrida* 'PHALEMWAS', not patented. In side-by-side comparisons, plants of the new *Phalaenopsis* differ primarily from plants of 'PHALEMWAS' in the following characteristics:

1. Leaves of plants of the new *Phalaenopsis* are horizontal in aspect whereas leaves of plants of 'PHALEMWAS' are semi-drooping to drooping in aspect.
2. Leaf apices of plants of the new *Phalaenopsis* are obtuse whereas leaf apices of plants of 'PHALEMWAS' are acute.
3. Petals of plants of the new *Phalaenopsis* do not have any stripes whereas petals of plants of 'PHALEMWAS' are moderately striped.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA899665' grown in a container.

Figure 2:
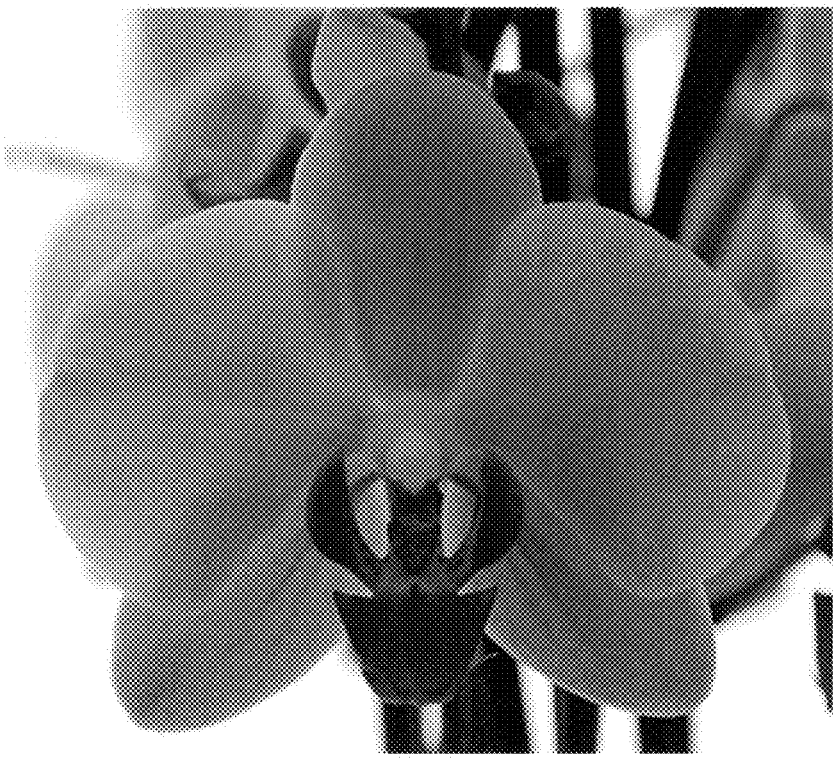

The photograph on the second sheet (FIG. 2) is a close-up view of a typical flower of 'PHA899665'.

DETAILED BOTANICAL DESCRIPTION

The aforementioned photographs and following observations and measurements describe plants grown during the late winter and early spring in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA899665'.

Parentage:

*Female, or seed, parent*.—Proprietary selection of *Phalaenopsis hybrida* identified as code number 10-44838-02, not patented.

*Male, or pollen, parent*.—Proprietary selection of *Phalaenopsis hybrida* identified as code number 99-21232-04, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; sparse.

Plant description:

*Plant form and growth habit*.—Herbaceous epiphyte; upright plant habit with typically three inflorescences developing per plant, each inflorescence with numerous flowers; monopodial; vigorous growth habit and moderate to rapid growth rate.

*Plant height, substrate level to top of foliar plane*.—About 23.8 cm.

*Plant height, substrate level to top of floral plane*.—About 57.6 cm.

*Plant diameter or spread*.—About 33.7 cm.

Leaf description:

*Arrangement and quantity*.—Distichous, simple; sessile; about four to six fully-developed leaves per plant.

*Length*.—About 24.9 cm.

*Width*.—About 8.6 cm.

*Aspect*.—Horizontal.

*Shape*.—Narrowly oblong to oblanceolate; slightly carinate.

*Apex*.—Unequal obtuse.

*Base*.—Sheathing. Sheath length: About 2.3 cm. Sheath width: About 1.7 cm. Sheath color: Close to 143B and 144B, moderately to strongly tinged with close to N186C.

*Margin*.—Entire; not undulate.

*Texture and luster, upper and lower surfaces*.—Smooth, glabrous; moderately glossy.

*Venation pattern*.—Camptodromous.

*Color*.—Developing leaves, upper surface: Close to a blend of NN137B and 146A. Developing leaves, lower surface: Close to 146A and strongly tinged with close to 200A. Fully expanded leaves, upper surface: Close to a blend of NN137B and 146A; venation, close to a blend of NN137A and 139A. Fully expanded leaves, lower surface: Close to 146A; towards the margins, slightly tinged with close to 200A; venation, close to NN137A.

Inflorescence description:

*Appearance and flowering habit*.—Showy zygomorphic flowers arranged on axillary simple or branched racemes; typically three inflorescences develop per plant; each inflorescence with about 20 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about 14 weeks on the plant; flowers not persistent.

*Inflorescence length* (*lowermost flower to inflorescence apex*).—About 42 cm.

*Inflorescence width*.—About 19.7 cm.

*Flower buds*.—Height: About 1.9 cm. Diameter: About 1.3 cm by 1.6 cm. Shape: Broadly ovate. Color: Close to N144A and 144B; towards the apex, tinged with close to 175A.

*Flower size*.—About 6.8 cm (vertical) by 7.7 cm (horizontal).

*Flower depth*.—About 2.9 cm.

*Petals, quantity and arrangement*.—Three, two lateral petals and one center petal transformed into a labellum.

*Lateral petals*.—Length: About 3.5 cm. Width: About 4.1 cm. Shape: Broadly deltoid-reniform. Apex: Shallow and broadly retuse. Margin: Entire; not undulate. Texture and luster, upper and lower surfaces: Smooth, glabrous, moderately velvety; matte. Color: When opening, upper surface: Close to 4A and 5B; at the base, tinged with close to 34C to 34D. When opening, lower surface: Close to 2B; main vein, close to N34C. Fully opened, upper surface: Close to 4B; at the base, tinged with close to 54C; color does not change with subsequent development. Fully opened, lower surface: Close to 4B; centers, close to 4C; at the base, slightly tinged with close to 54C; main vein, tinged with close to N34C; color does not change with subsequent development.

*Labella*.—Appearance: Three-parted with two lateral lobes and a central lobe. Length, lateral lobes: About 2.1 cm. Width, lateral lobes: About 1 cm. Length, central lobe: About 2.1 cm. Width, central lobe: About 6 mm to 19 mm. Length, cirrhose tips: About 1 cm. Shape, lateral lobes: Narrowly obovate. Shape, central lobe: Rhomboidal with a slightly elongated apex. Apex, lateral lobes: Obtuse. Apex, central lobe: Minutely and broadly acute two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 5 mm in height. Color: When opening, upper surface: Lateral lobes: Close to 70A; towards the apex, close to 70B; lower margins, strongly tinged with close to 173B; at the base, close to 155C; base and upper half with axial stripes, close to 172B. Central lobe: Close to 184C; margins of broad portion of lobe, close to 164B; at the base, close to 2D and 71B with radial stripes, close to 185A; cirrhose tips, close to 70A. Callosities: Close to 2D; towards the apex, close to 13B; fine dots, close to 185A. When opening, lower surface: Lateral lobes: Close to 59D, 70C and 70D; towards the lower margins, strongly tinged with close to 173B; at the base, close to 160D. Central lobe: Close to 182B and 182C; margins of broad portion of lobe, tinged with close to 161A; at the base, close to 2D; cirrhose tips, close to 70A. Fully opened, upper surface: Lateral lobes: Close to 70A; towards the apex, close to 70B; lower margins, strongly tinged with close to 173B; at the base, close to 155A; base and upper half with axial stripes, close to 172B. Central lobe: Close to 184C; margins of broad portion of lobe, close to 164B; at the base, close to 2D and 71B with radial stripes, close to 185A; cirrhose tips, close to 70A. Callosities: Close to 2D; towards the apex, close to 13B; fine dots, close to 185A. Fully opened, lower surface: Lateral lobes: Close to 59D, 70C and 70D; towards the lower margins, strongly tinged with close to 173B; at the base, close to 160D. Central lobe: Close to 70B; margins of broad portion of lobe, tinged with close to 161A; at the base, close to 155A; cirrhose tips, close to 70A.

*Sepals*.—Quantity and arrangement: Three, one upper dorsal sepal and two lower lateral sepals. Length, dorsal sepal: About 3.8 cm. Width, dorsal sepal: About 2.7 cm. Length, lateral sepals: About 3.8 cm. Width, lateral sepals: About 2.6 cm. Shape, dorsal sepal: Broadly elliptic to slightly obovate. Shape, lateral sepals: Ovate. Apex, dorsal sepal: Obtuse to shallowly retuse. Apex, lateral sepals: Bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 153D. When opening, lower surface: Close to 151B, moderately to strongly tinged with close to 165A; towards the margins, close to a blend of 1A and 151C. Fully opened, upper surface: Close to 5C and 6D; at the base, slightly tinged with close to 54D. Fully opened, lower surface: Close to 151C, slightly to moderately tinged with close to 164A; towards the margins, close to 154C. Color, lateral sepals: When opening, upper surface: Close to a blend of 2A, 151B and 151C; towards the base, close to 153D; proximal venation, close to 180A. When opening, lower surface: Close to 151B and 151C, moderately to strongly tinged with close to 165A. Fully opened, upper surface: Close to 1C and 2C; towards the base, close to a blend of 5C and 151D; proximal venation, close to 181A. Fully opened, lower surface: Close to 154C, slightly to moderately tinged with close to 164A.

*Peduncles*.—Length: About 61 cm. Diameter: About 6 mm. Strength: Strong. Aspect: Upright to outwardly arching. Texture and luster: Smooth, glabrous; matte. Color: Close to 200A; heavily dotted with fine dots, close to 147B.

*Pedicels*.—Length: About 5 cm. Diameter: About 2.75 mm. Strength: Moderately strong. Aspect: About 65° from peduncle axis. Texture and luster: Smooth, glabrous; matte. Color: Close to 146D; proximally, close to N199A and distally, close to 199D.

*Reproductive organs*.—Androecium: Column length: About 8 mm. Column width: About 6 mm. Column color: Close to NN155B. Pollinia quantity: Two. Pollinia diameter (per two pollinia): About 3 mm. Pollinia color: Close to 23A. Gynoecium: Stigma length: About 3 mm. Stigma width: About 5 mm. Stigma shape: Reniform. Stigma color: Close to 155C. Ovary length: About 1.2 cm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA899665' as herein illustrated and described.

* * * * *